United States Patent
Wu et al.

(10) Patent No.: US 10,765,357 B2
(45) Date of Patent: Sep. 8, 2020

(54) SYSTEM AND METHOD FOR DETECTING MUSCLE ACTIVITIES

(71) Applicant: INDUSTRIAL TECHNOLOGY RESEARCH INSTITUTE, Hsinchu (TW)

(72) Inventors: Chi-Kang Wu, Taipei (TW); Cheng-Li Chang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 259 days.

(21) Appl. No.: 14/981,846

(22) Filed: Dec. 28, 2015

(65) Prior Publication Data
US 2017/0172491 A1    Jun. 22, 2017

(30) Foreign Application Priority Data
Dec. 17, 2015  (TW) .............................. 104142516 A (51) Int. Cl.
*A61B 5/00*  (2006.01)
*A61B 5/11*  (2006.01)
*G06F 3/01*  (2006.01)

(52) U.S. Cl.
CPC .............. *A61B 5/4519* (2013.01); *A61B 5/11* (2013.01); *A61B 5/1107* (2013.01); *A61B 5/1123* (2013.01); *A61B 5/6824* (2013.01); *A61B 5/7225* (2013.01); *A61B 5/7282* (2013.01); *A61B 2505/09* (2013.01); *A61B 2562/0219* (2013.01); *A61B 2562/04* (2013.01); *G06F 3/01* (2013.01); *G06F 3/015* (2013.01); *G06F 3/017* (2013.01)

(58) Field of Classification Search
CPC ... A61B 5/4519; A61B 5/1107; A61B 5/1123; A61B 5/6824; A61B 2562/0219; G06F 3/01; G06F 3/015; G06F 3/017
See application file for complete search history.

(56) References Cited

U.S. PATENT DOCUMENTS

| | | | |
|---|---|---|---|
| 4,580,569 A | 4/1986 | Petrofsky | |
| 4,855,942 A | 8/1989 | Bianco | |
| 5,368,042 A | 11/1994 | O'Neal et al. | |
| 6,344,062 B1 | 2/2002 | Abboudi et al. | |
| 7,593,776 B2 | 9/2009 | Loeb et al. | |

(Continued)

FOREIGN PATENT DOCUMENTS

| | | |
|---|---|---|
| CN | 102499797 A | 6/2012 |
| CN | 103558918 A | 2/2014 |

(Continued)

OTHER PUBLICATIONS

Scheeren et al. "Wrist Movement Characterization by Mechanomyography Technique", Journal of Medical and Biological Engineering, vol. 30, No. 6, 2010, pp. 373-380. (Year: 2010).*

(Continued)

*Primary Examiner* — Devin B Henson
(74) *Attorney, Agent, or Firm* — Rabin & Berdo, P.C.

(57) ABSTRACT

A system and a method for detecting a muscle activity are provided. The system includes a vibration sensor. The vibration sensor detects a vibration signal at a sensing point located at an opposite side of an operating muscle system for analyzing a body movement.

13 Claims, 11 Drawing Sheets

(56) References Cited

U.S. PATENT DOCUMENTS

| | | | |
|---|---|---|---|
| 7,755,602 | B2 | 7/2010 | Tremblay et al. |
| 8,170,656 | B2 | 5/2012 | Tan et al. |
| 8,447,704 | B2 | 5/2013 | Tan et al. |
| 2009/0327171 | A1 | 12/2009 | Tan et al. |
| 2011/0028819 | A1 | 2/2011 | Eger et al. |
| 2011/0230783 | A1 | 9/2011 | Bartol et al. |
| 2012/0004578 | A1 | 1/2012 | Wu et al. |
| 2012/0157886 | A1 | 6/2012 | Tenn et al. |
| 2013/0165813 | A1 | 6/2013 | Chang et al. |
| 2014/0163412 | A1* | 6/2014 | Jacobson ............ A61B 5/0488 600/546 |
| 2014/0198034 | A1 | 7/2014 | Bailey et al. |
| 2014/0198035 | A1 | 7/2014 | Bailey et al. |
| 2014/0240103 | A1 | 8/2014 | Lake et al. |
| 2014/0240223 | A1 | 8/2014 | Lake et al. |
| 2015/0025355 | A1 | 1/2015 | Bailey et al. |
| 2015/0057841 | A1 | 2/2015 | Hsu et al. |
| 2015/0065090 | A1 | 3/2015 | Yeh |
| 2017/0231506 | A1* | 8/2017 | Simpson ................ A61B 5/11 600/481 |

FOREIGN PATENT DOCUMENTS

| | | |
|---|---|---|
| CN | 103869942 A | 6/2014 |
| CN | 104267807 A | 1/2015 |
| TW | 476643 B | 2/2002 |
| TW | 200740410 A | 11/2007 |
| TW | M471576 U | 2/2014 |
| TW | M478858 U | 5/2014 |
| WO | WO 2015-033327 A1 | 3/2015 |
| WO | WO 2015-102713 A2 | 7/2015 |

OTHER PUBLICATIONS

Chin-hua Wang et al., "Application of MMG's Scientific Researches", TPEC Press, vol. 15, pp. 348-358, Nov. 1, 2007.

Jhih-ming Wu, "Electomyography and mechanomyography during incremental step exercise", Master's Thesis of National College of Physical Education and Sports Taiwan Republic of China, 2004.

Taiwanese Office Action dated Sep. 12, 2016.

Taiwanese Office Action dated Dec. 25, 2014.

P. Madeleine et al., "Mechanomyography and electromyography force relationships during concentric, isometric and eccentric contractions", Journal of Electromyography and Kinesiology, vol. 11, Issue 2, pp. 113-121, Apr. 2001.

Artur Jaskólski et al., "Similar response of agonist and antagonist muscles after eccentric exercise revealed by electromyography and mechanomyography", Journal of Electromyography and Kinesiology, vol. 17, Issue 5, pp. 568-577, Oct. 2007.

Liping Qi et al., "Spectral properties of electromyographic and mechanomyographic signals during dynamic concentric and eccentric contractions of the human biceps brachii muscle", Journal of Electromyography and Kinesiology, vol. 21, Issue 6, pp. 1056-1063, Dec. 2011.

Natasha Alves et al., "Uncovering patterns of forearm muscle activity using multi-channel mechanomyography", Journal of Electromyography and Kinesiology, vol. 20, Issue 5, pp. 777-786, Oct. 2010.

Travis W Beck et al., "Mechanomyographic amplitude and frequency responses during dynamic muscle actions: a comprehensive review", BioMedical Engineering OnLine, Dec. 19, 2005.

Isa Conradsen et al., "Multi-modal Intelligent Seizure Acquisition (MISA) system—a new approach towards seizure detection based on full body motion measures", 31st Annual International Conference of the IEEE EMBS, pp. 2591-2595, Sep. 2-6, 2009.

* cited by examiner

SYSTEM AND METHOD FOR DETECTING MUSCLE ACTIVITIES

CROSS-REFERENCE TO RELATED APPLICATIONS

This non-provisional application claims priority under 35 U.S.C. § 119(a) on Patent Application No. 104,142,516 filed in Taiwan on Dec. 17, 2015, the entirety of which is incorporated herein by reference.

BACKGROUND OF THE DISCLOSURE

Field of the Disclosure

This disclosure relates to a method and a system for detecting muscle activity.

BACKGROUND OF THE DISCLOSURE

With the development of technologies, the integration of the biotechnology and the electromechanical technology provides a variety of emerging applications. For example, detecting the muscle activity and analyzing the changes in body movements, thus can apply these body movements to game control, presentation control and appliance control.

Nowadays, an Electromyogram (EMG) signal is primarily used for detection of the muscle activity. Muscle contraction will generate an action potential. The greater the contraction amplitude is, the larger the action potential will be. The EMG signal records the changes in the action potential of an operating agonist muscle system. Here, the operating agonist muscle system is a muscle system which includes muscle cells, connective tissue, blood vessel, nerve fibers, etc.

However, when the user sweats, measuring the EMG signal is affected easily. Moreover, the EMG signal should be measured in a large enough area.

SUMMARY

A muscle activity detection system is provided, which comprises a first vibration sensor. The first vibration sensor detecting a first vibration signal at a first sensing point located at an opposite side of a first agonist muscle system for analyzing a body movement.

A method for detecting a muscle activity adapted to a muscle activity detection system is provided, which comprises: detecting a first vibration signal at a first sensing point located at an opposite side of a first agonist muscle system.

Further scope of applicability of the present disclosure will become apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure.

DESCRIPTION OF THE EMBODIMENTS

The present disclosure will now be described in detail with reference to the accompanying drawings, wherein the same reference numerals will be used to identify the same or similar elements throughout the several views. It should be noted that the drawings should be viewed in the direction of orientation of the reference numerals.

In one embodiment, the muscle activity detection system includes a vibration sensor. The vibration sensor detects the muscle activity by sensing a vibration signal generated by the muscle. The vibration signal, for example, is a Mechanomyography (MMG) signal.

Please refer to Table I, which shows the comparison chart of the EMG signal and the vibration signal (e.g. MMG signal).

TABLE I

|  | EMG signal | vibration signal (e.g. MMG signal) |
| --- | --- | --- |
| type | voltage signal | vibration signal |
| sensor | metal electrode and amplifier that are complying with medical regulations | sound reception device, inertial sensing element or piezoelectric sensing element |
| medical value stability | Meaningful to the Neurophysiology significance affected by sweating | able to detect partial of fatigue and muscle status not affected by skin conditions |
| Signal frequency | ≥500 Hz | approximate to 5~100 Hz |
| Material restrictions | unable to use metal | can be covered with perspiration or soft materials |

TABLE I-continued

| | EMG signal | vibration signal (e.g. MMG signal) |
|---|---|---|
| Space limitation | require a large enough area | able to measure a smaller area |
| cost | high | low |

According to the comparison of the EMG signal and the MMG signal in table I, it may be seen that there are advantages when using the vibration signal for detecting the muscle activity. The vibration sensor is not easily affected by the skin sweating, and the vibration signal is applicable to movement analysis or rehabilitation analysis. In addition, the vibration signal has a lower frequency, therefore, it has a lower traffic load and a lower power consumption. Furthermore, the vibration sensor can be covered with perspiration material or soft material, thus increasing the user's comfort. In addition, the vibration sensor can be made thinner, lighter and conducive to facilitate being integrated in a wearable device.

Figure 1A:
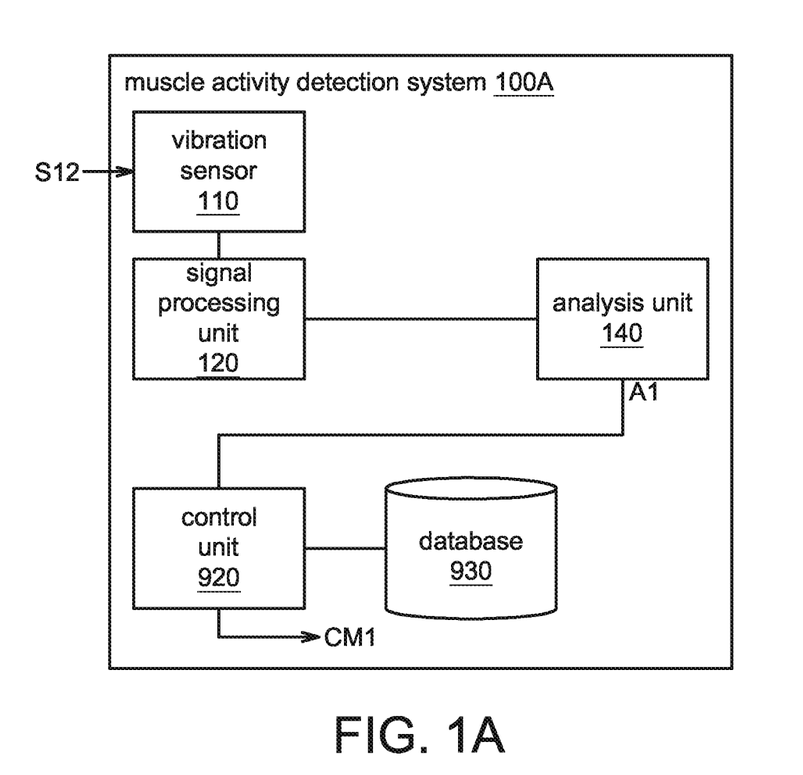
FIG. 1A shows a block diagram of a muscle activity detection system according to an exemplary embodiment.

FIG. 1A shows a block diagram of a muscle activity detection system 100A according to an exemplary embodiment. The muscle activity detection system 100A comprises a vibration sensor 110, a signal processing unit 120, an analysis unit 140, a control unit 920 and a database 930. The vibration sensor 110 is configured to sense a vibration signal. The vibration sensor 110 may be, but not limited to, a sound reception device, an inertial sensing element or a piezoelectric sensing element. The signal processing unit 120 comprises, for example, an analog-to-digital converter (ADC) and a filter. The analog-to-digital converter is configured to convert analog signals to digital signals. The analog-to-digital converter may be, but not limited to, a chip, a circuit or a circuit board. The filter is configured to filter partial frequency or to retain some frequency. The filter may be, but not limited to, a chip, a circuit or a circuit board. The analysis unit 140 is configured to perform analyzing, calculating and determining procedures. The analysis unit 140 maybe, but not limited to, a chip, a circuit, a circuit board, or a storage device for storing programs. The control unit 920 is configured to perform controlling procedures. The control unit 920 may be, but not limited to, a chip, a circuit, a circuit board, or a storage device for storing programs. The database 930 is configured to store data. The database 930 may be, but not limited to, a hard disk, a memory, a portable storage device, or a cloud storage device.

Figure 1B:
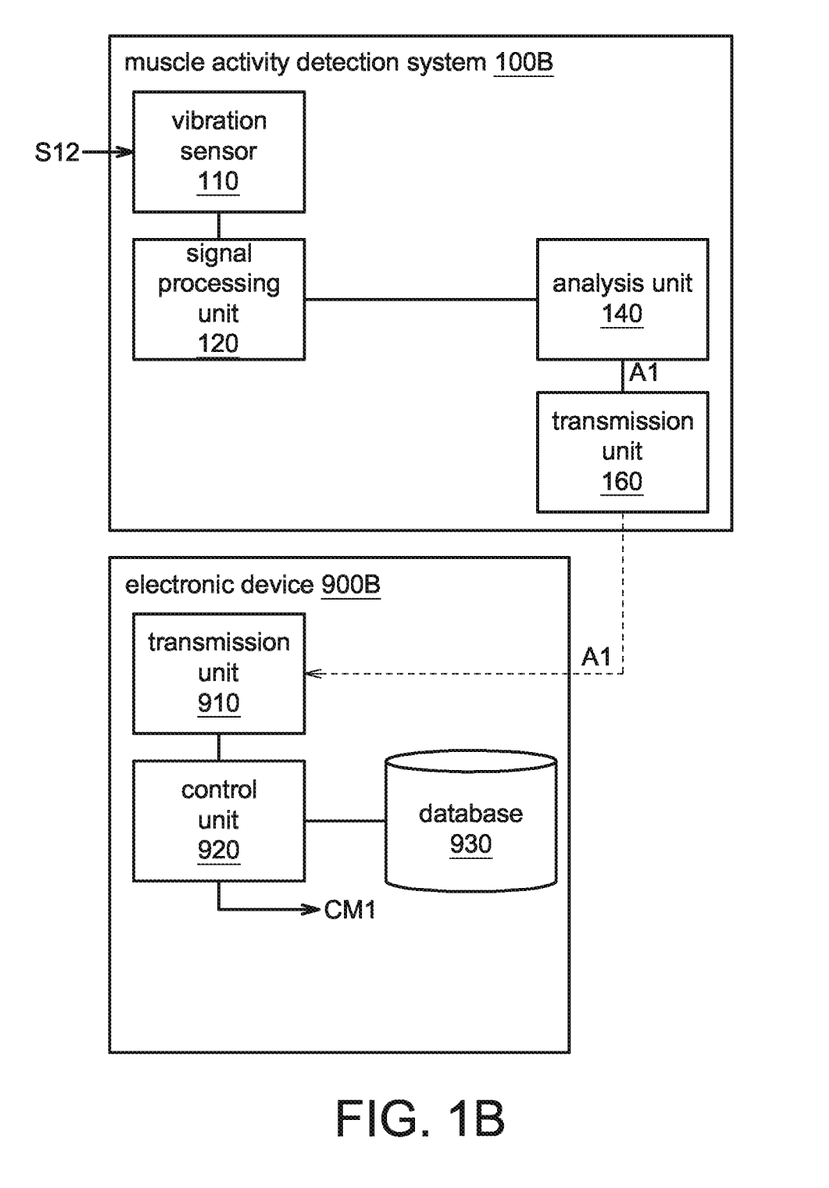
FIG. 1B shows a block diagram of a muscle activity detection system according to another exemplary embodiment.

FIG. 1B shows a block diagram of a muscle activity detection system 100B and an electronic device 900B according to another exemplary embodiment. The muscle activity detection system 100B for example is a wearing device. The electronic device 900B for example is a mobile, a computer or a fitness equipment. The muscle activity detection system 100B comprises a vibration sensor 110, a signal processing unit 120, analysis unit 140 and a transmission unit 160. The electronic device 900B comprises a transmission unit 910, a control unit 920 and a database 930. The transmission unit 160 and the transmission unit 910 may be, but not limited to, a wireless transceiver module, a Bluetooth transceiver module, or a transmission line.

Figure 1C:
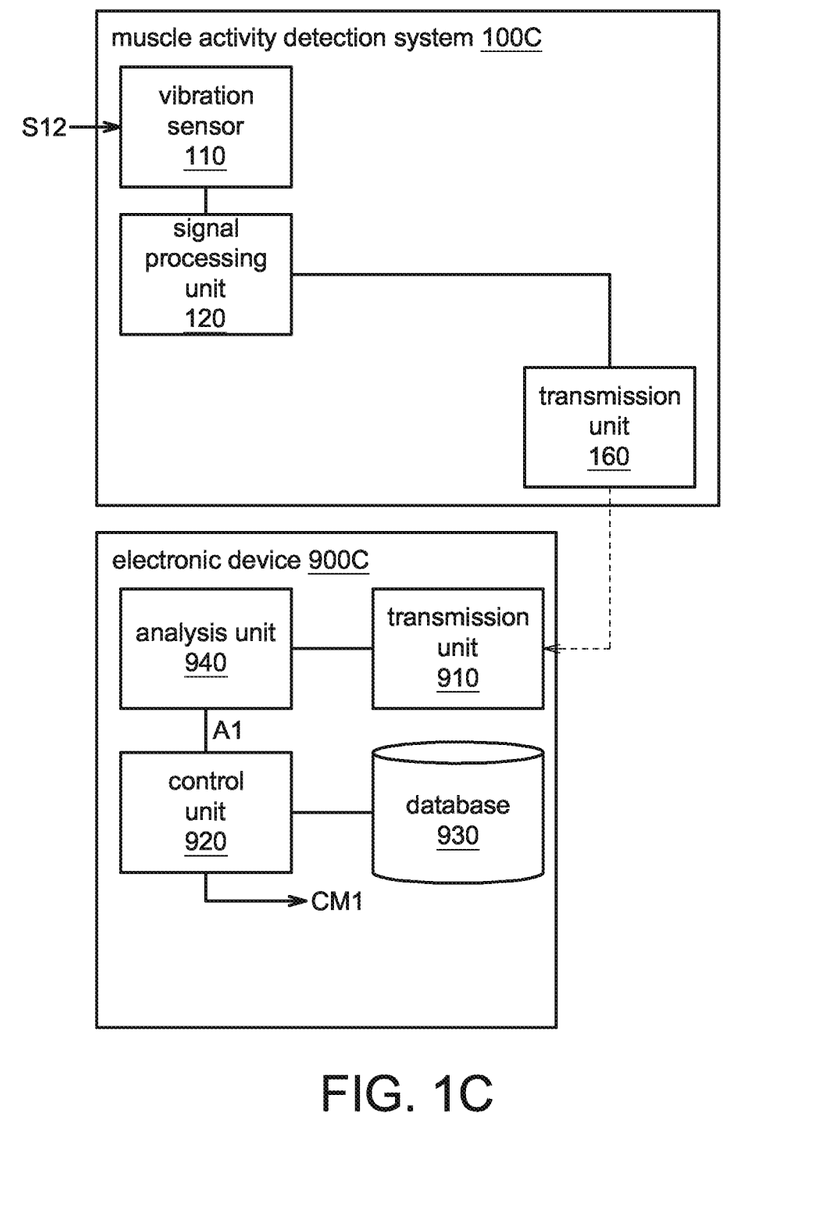
FIG. 1C shows a block diagram of a muscle activity detection system according to another exemplary embodiment.

FIG. 1C shows a block diagram of a muscle activity detection system 100C and an electronic device 900C according to another exemplary embodiment. The muscle activity detection system 100C, for example, is a wearing device. The electronic device 900C for example is a mobile, a computer or a fitness equipment. The muscle activity detection system 100C comprises a vibration sensor 110, a signal processing unit 120 and a transmission unit 160. The electronic device 900C comprises a transmission unit 910, an analysis unit 940, a control unit 920 and a database 930. The transmission unit 160 and the transmission unit 910 may be, but not limited to, a wireless transceiver module, a Bluetooth transceiver module, or a transmission line.

Figure 2:
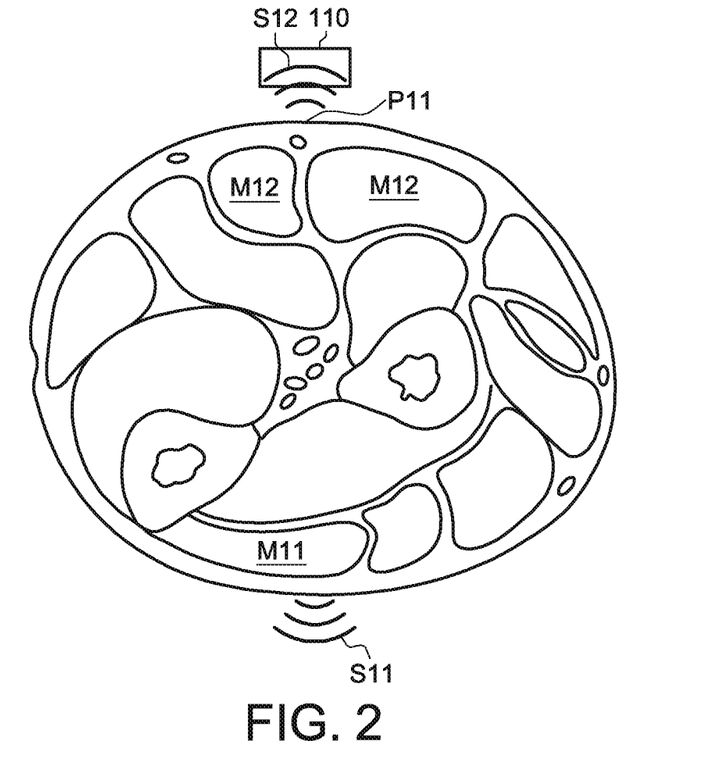
FIG. 2 shows a muscle cross-sectional view according to an exemplary embodiment.

FIG. 2 shows a muscle cross-sectional view according to an exemplary embodiment. In embodiments, the vibration sensor 110 is located at a sensing point P11 which is at the opposite side of an agonist muscle system M11, for example, it is located at an antagonistic muscle group M12 corresponding to the agonist muscle system M11. When the agonist muscle system M11 contracts, the friction between the muscle fibers of the agonist muscle system M11 and the friction between the agonist muscle system M11 and serous membrane will generate a vibration signal S11. Corresponding to the muscle contraction, the antagonistic muscle group M12 will result in eccentric contraction. The friction between the muscle fibers of the antagonistic muscle group M12 and the friction between the antagonistic muscle group M12 and serous membrane will generate a vibration signal S12. For a long time, the technical prejudice is sensing at the force point of the agonist muscle system M11 can detect the muscle activity, and if the vibration sensor is near the agonist muscle system M11, it can gain a better sensing result. After a hard research, it is known that the amplitude of the vibration signal S12 is triple of the amplitude of the vibration signal S11, and the sensing point located at the antagonistic muscle group M12 can result in a good effect. This research result is an important breakthrough for detecting the muscle activity by using the vibration signal.

In addition, for a long time, the technical prejudice is the detection can become more accurate if more sensors are used. However, the research result also shows that a plurality of vibration sensors easily interfere with each other, and this affects the accuracy of detection. Instead, reducing the number of vibration sensors and locating the vibration sensors appropriately can improve the accuracy of detection.

Figure 3:
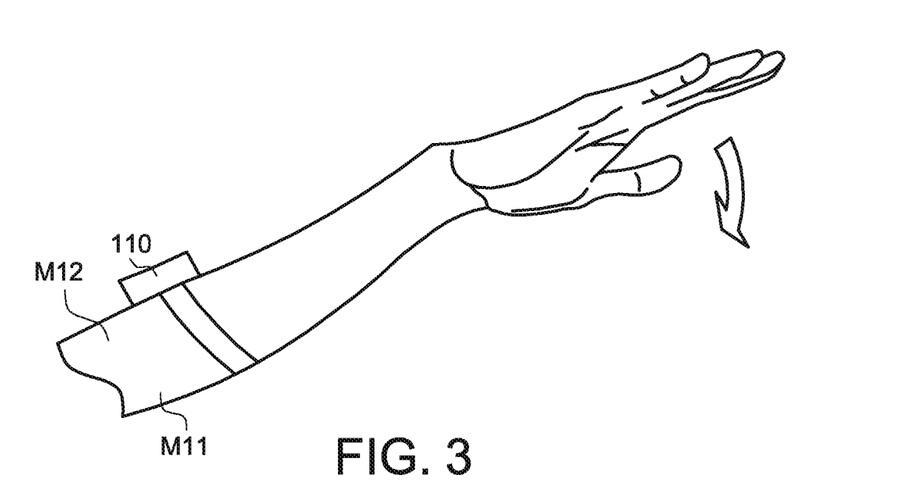
FIG. 3 shows a schematic diagram of the arm and the palm according to another exemplary embodiment.

FIG. 3 shows a schematic diagram of the arm and the palm according to an exemplary embodiment. Corresponding to the contraction of the agonist muscle system M11 below the arm, the antagonistic muscle group M12 corresponding to the agonist muscle system M11 will result in an eccentric contraction, so the palm swings down. The user may wear the vibration sensor on the outside of the arm, it can successfully detect the palm's downward swing movement.

In one embodiment, the vibration sensor is located at the sensing point P11 which is at the opposite side of the agonist muscle system M11, as shown in FIG. 2. The vibration sensor senses the vibration signal S12 which provides information for analyzing the body movement.

Figure 4:
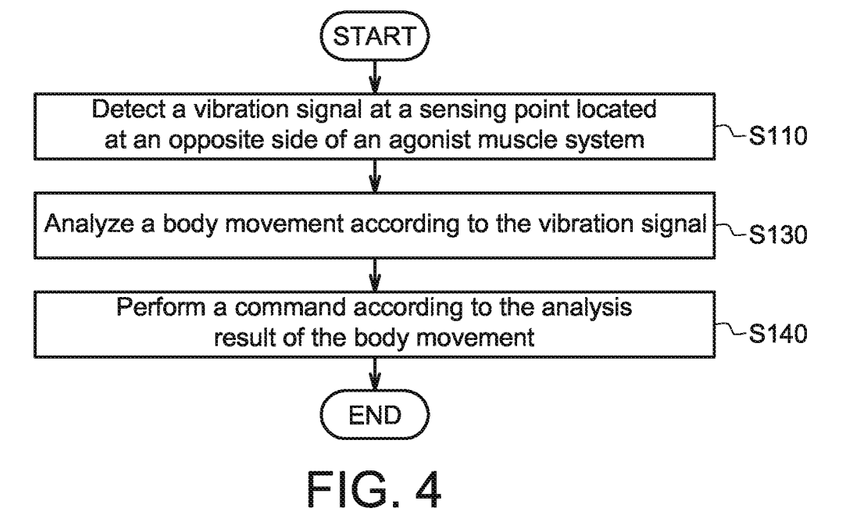
FIG. 4 shows a method of detecting the muscle activity according to an exemplary embodiment.

FIG. 4 shows a method of detecting the muscle activity according to an exemplary embodiment. The following accompanies with the flowchart in FIG. 4 to describe the operations of the muscle activity detection systems 100A~100C in FIG. 1A~FIG. 1C. However, the operations of the muscle activity detection systems 100A~100C are not limited to using the flowchart in FIG. 4. The method for detecting a muscle activity (shown in FIG. 4) is not limited to being performed in the muscle activity detection systems 100A~100C in FIG. 1A~FIG. 1C.

Here, FIG. 1A is taken as an example for illustration. In step S110, the vibration sensor 110 detects the vibration signal S12 at a sensing point P11 located at an opposite side of an agonist muscle system M11. As described above, the vibration signal is generated primarily by the antagonistic muscle group M12 at the opposite side of the agonist muscle system M11.

The vibration signal S12 is converted from an analog signal into a digital signal by the analog-to-digital converter of the signal processing unit 120, and the noises outside 5~100 Hz are filtered by the filter. The operations of the analog-to-digital converting and the noise filtering are changeable without limitations on the operation order.

In step S130, the analysis unit 140 analyzes a body movement according to the vibration signal S12. In this step, the analysis unit 140 performs the analysis according to signal feature(s) of the vibration signal S12. The signal feature(s) may comprise, for example, but not limited to, at least one of an amplitude and a frequency.

In the muscle activity detection system 100A (shown in FIG. 1A), an analysis result A1 of the body movement may be transmitted to the control unit 920 directly. In the muscle activity detection system 100B (shown in FIG. 1B), the analysis result A1 of the body movement may be transmitted to the transmission unit 910 of the electronic device 900B by the transmission unit 160, and is further transmitted to the control unit 920 of the electronic device 900B. In the muscle activity detection system 1000 (as shown in FIG. 1C), the signal processed by the signal processing unit 120 may be transmitted to the transmission unit 910 of the electronic device 900C by the transmission unit 160, and is further transmitted to the analysis unit 940 of the electronic device 900C. The analysis unit 940 analyzes the body movement according to the signal feature(s) of the vibration signal S12, and transmits the analysis result A1 of the body movement to the control unit 920.

In step S140, after the control unit 920 receives the analysis result A1 of the body movement, the control unit 920 performs a command CM1 according to the analysis result A1 of the body movement. The command CM1, such as turn off the television (TV), answer the phone, or turn off the screen.

In this step, a command mapping table which records the mappings of body movements and commands may be pre-stored in the database 930. The control unit 920 looks up the command CM1 in the command mapping table.

Figure 5A:
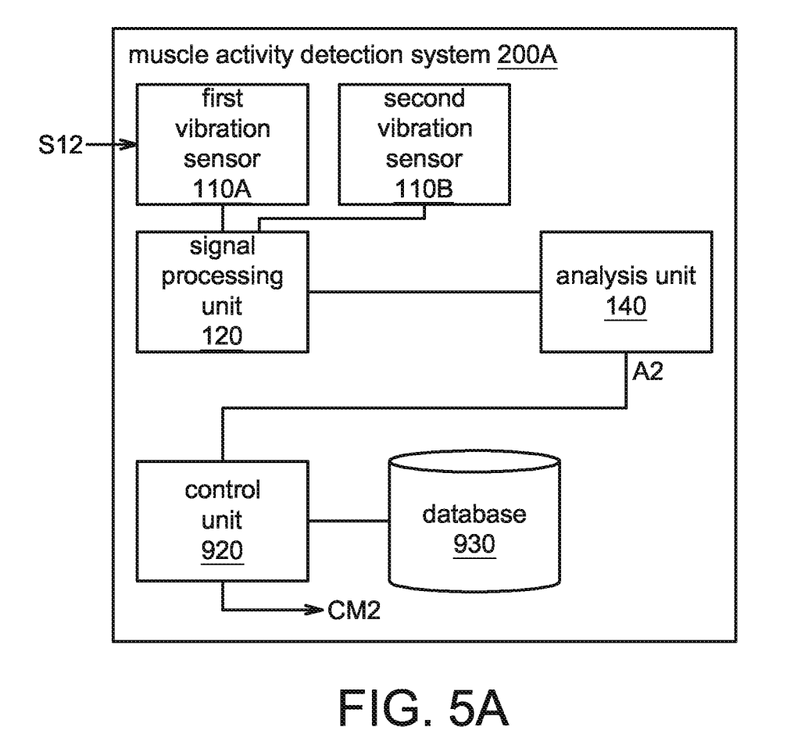
FIG. 5A shows a block diagram of a muscle activity detection system according to another exemplary embodiment.
Figure 5B:
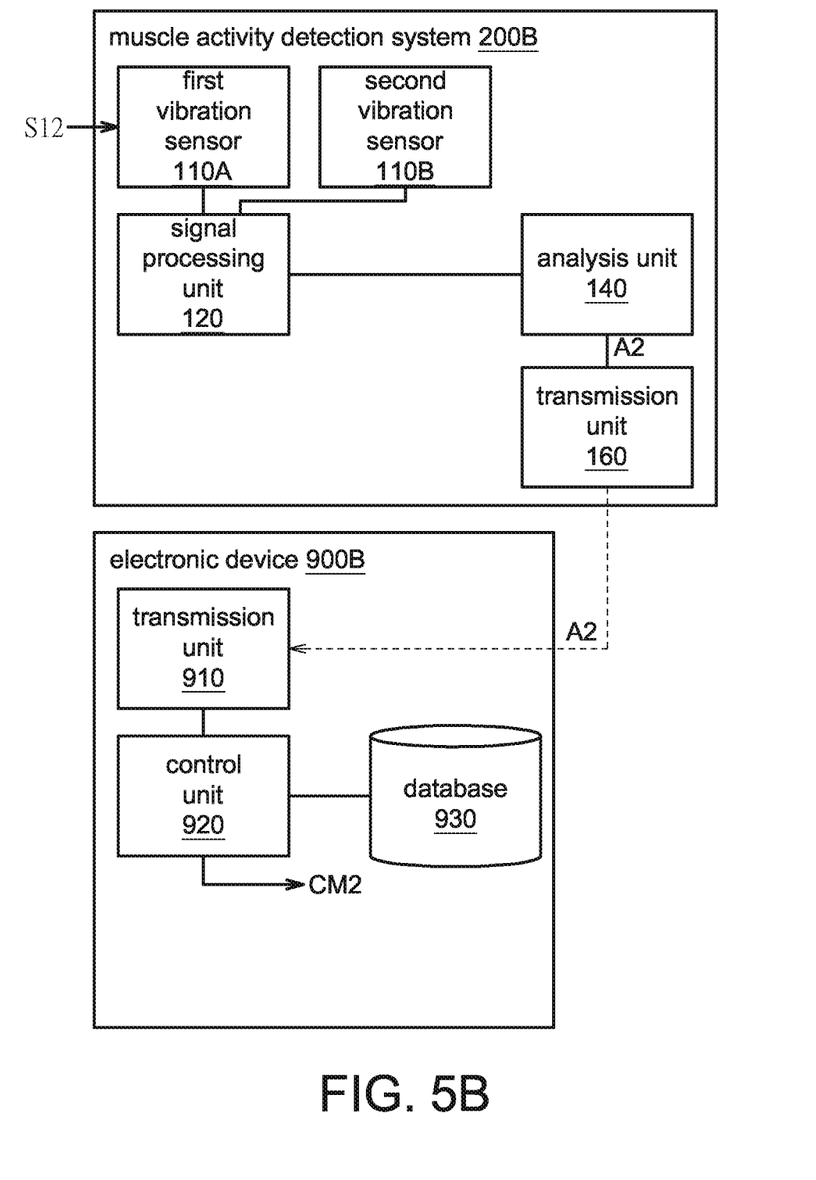
FIG. 5B shows a block diagram of a muscle activity detection system according to another exemplary embodiment.
Figure 5C:
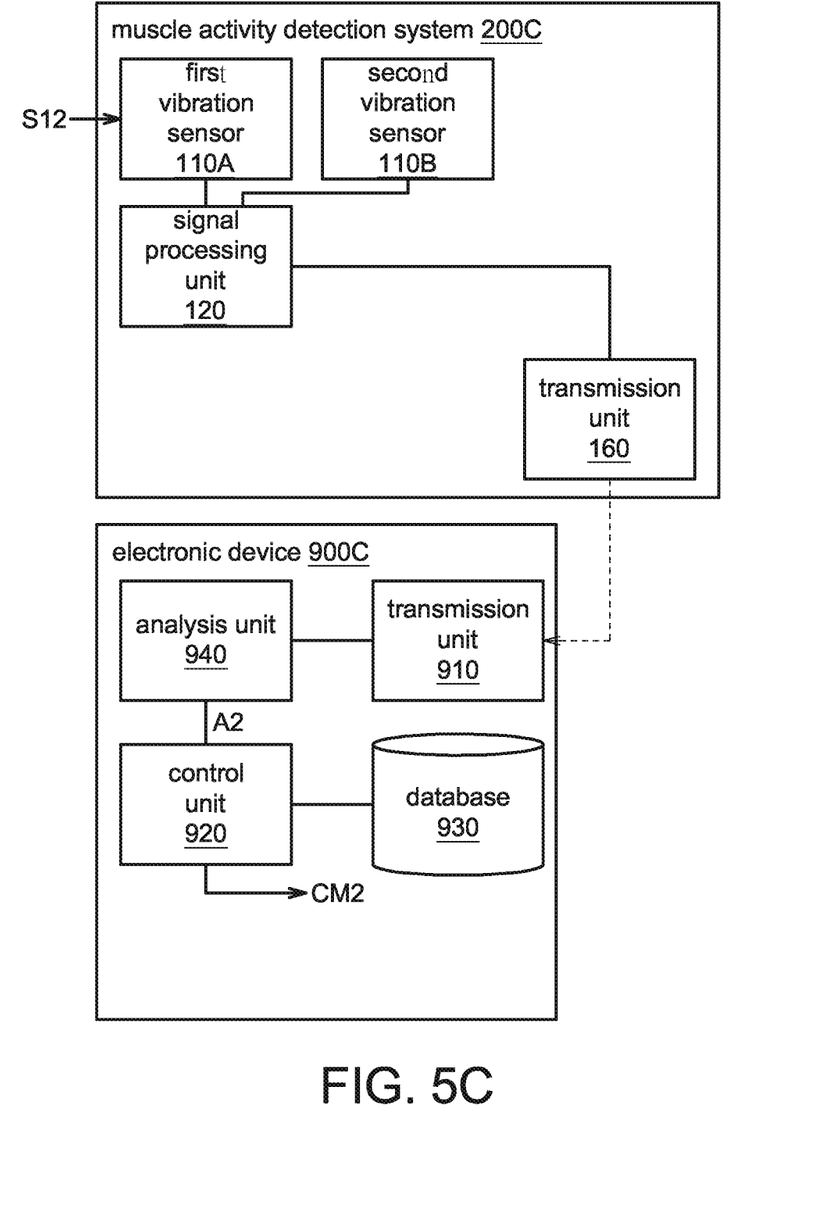
FIG. 5C shows a block diagram of a muscle activity detection system according to another exemplary embodiment.

FIG. 5A~FIG. 5C show block diagrams of the muscle activity detection systems 200A~200C, respectively, according to another exemplary embodiment. The difference between the muscle activity detection systems 200A~200C and the muscle activity detection systems 100A~100C is that the muscle activity detection systems 200A~200C include a first vibration sensor 110A and a second vibration sensor 110B.

Figure 6:
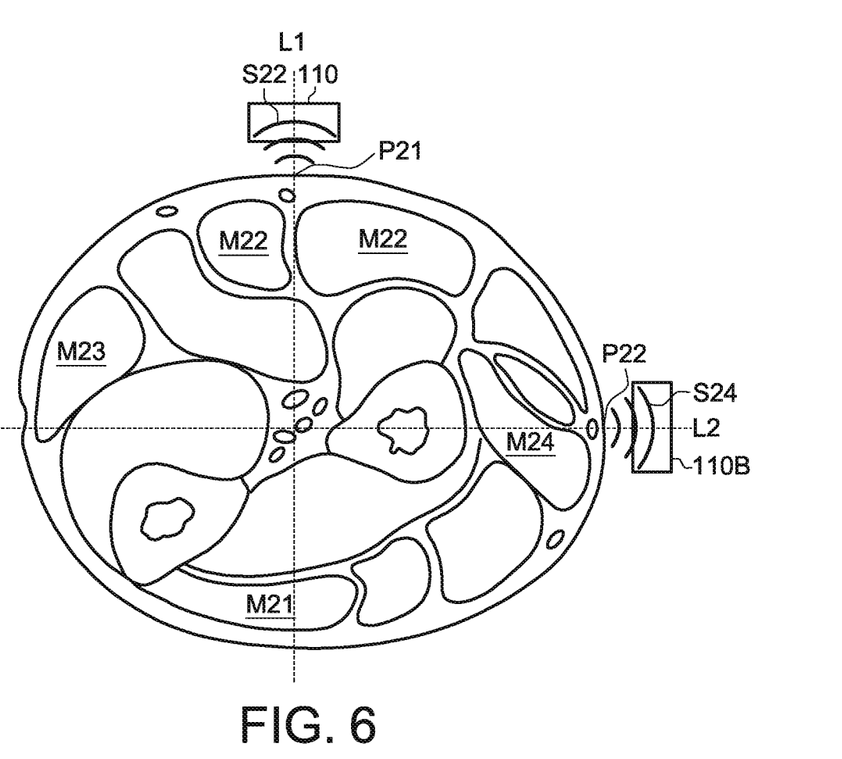
FIG. 6 shows a muscle cross-sectional view according to another exemplary embodiment.

FIG. 6 shows a muscle cross-sectional view according to another exemplary embodiment. The first vibration sensor 110A is located at a sensing point P21 which is at the opposite side of the first agonist muscle system M21. For example, the sensing point P21 is at the first antagonistic muscle group M22 corresponding to the first agonist muscle system M21. The second vibration sensor 110B is located at a sensing point P22 which is at the opposite side of the second agonist muscle system M23. For example, the sensing point P22 is at the second antagonistic muscle group M24 corresponding to the second agonist muscle system M23. When the first agonist muscle system M21 contracts, the first antagonistic muscle group M22 will result in an eccentric contraction. The friction between the muscle fibers of the first antagonistic muscle group M22 and the friction between the first antagonistic muscle group M22 and the serous membrane will generate the first vibration signal S22.

When the second agonist muscle system M23 contracts, the second antagonistic muscle group M24 will result in an eccentric contraction. The friction between the muscle fibers of the second antagonistic muscle group M24 and the friction between the second antagonistic muscle group M24 and the serous membrane will generate the second vibration signal S24.

In embodiments, the first agonist muscle system M21 is independent of the second antagonistic muscle group M24 when the first agonist muscle system M21 has an action, also, the second agonist muscle system M23 is independent of the first antagonistic muscle group M22 when the second agonist muscle system M23 has an action.

In embodiments, a first line L1 between the first agonist muscle system M21 and the first sensing point P21 is substantially perpendicular to a second line L2 between the second agonist muscle system M23 and the second sensing point P22. After research, it is found that when the first vibration sensor 110A and the second vibration sensor 110B are located at the perpendicular position, the interference between the first vibration sensor 110A and the second vibration sensor 110B is reduced. And, the accuracy of the detection is substantially increased.

Figure 7:
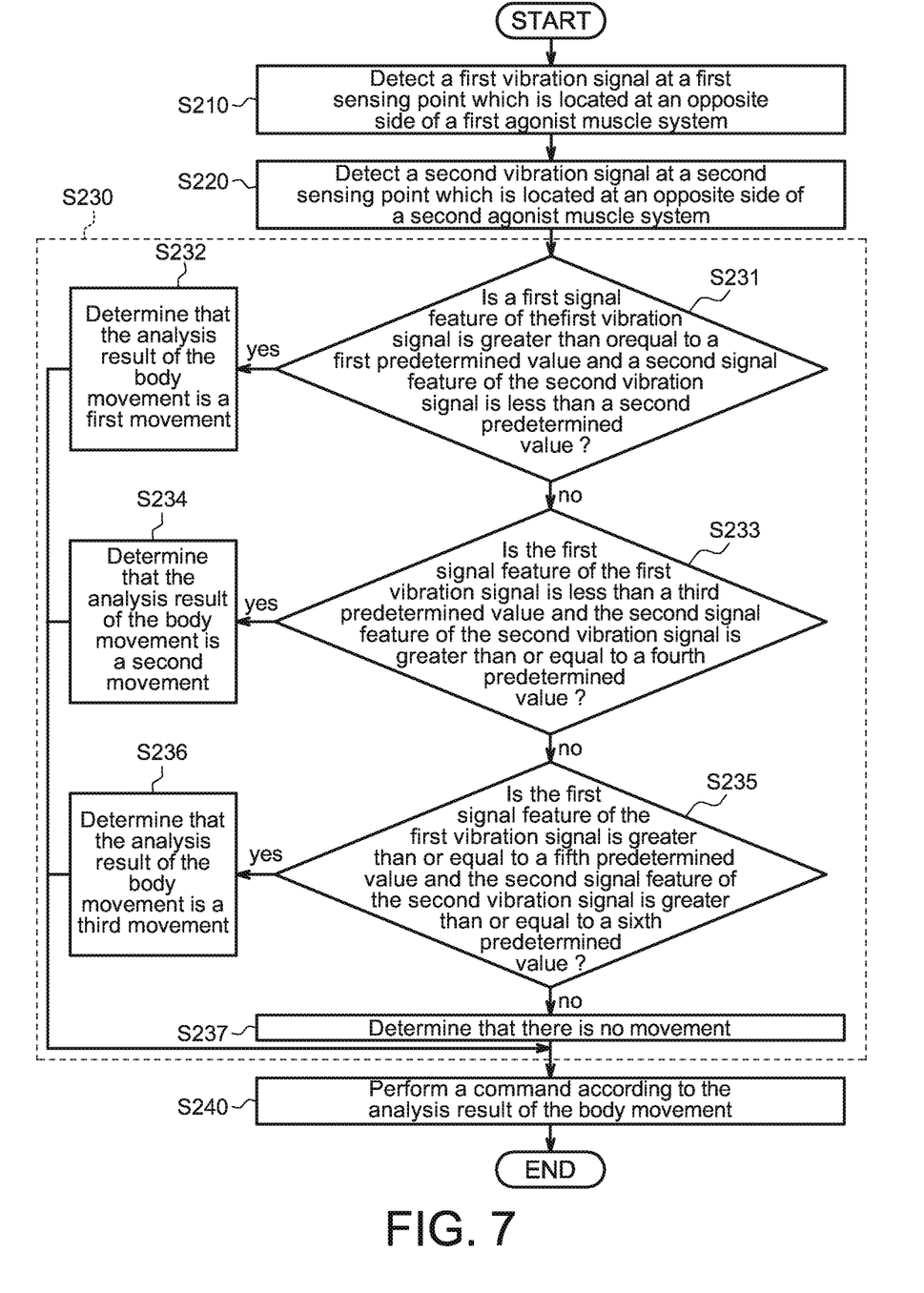
FIG. 7 shows a method of detecting muscle activity according to another exemplary embodiment.

FIG. 7 shows a method of detecting muscle activity according to another exemplary embodiment. The following accompanies with the flowchart in FIG. 7 to describe the operations of the muscle activity detection systems 200A~200C in FIG. 5A~FIG. 5C. However, the muscle activity detection systems 200A~200C are not limited to using the flowchart in FIG. 7. The method for detecting a muscle activity (shown in FIG. 7) is not limited to being performed in the muscle activity detection system 200A~200C in FIG. 5A~FIG. 5C.

In step S210, in one embodiment, the first vibration sensor 110A detects a first vibration signal S22 at a first sensing point P21 located at an opposite side of a first agonist muscle system M21 (shown in FIG. 6). As described above, the first vibration signal S22 is generated primarily by the first antagonistic muscle group M22 at the opposite side of the first agonist muscle system M21.

In step S220, in one embodiment, the second vibration sensor 110B detects the second vibration signal S24 at the second sensing point P22 which is located at an opposite side of the second agonist muscle system M23 (shown in FIG. 6). As described above, the second vibration signal S24 is not primarily generated by the second agonist muscle system M23, but is primarily generated by the second antagonistic muscle group M24 at the opposite side of the second agonist muscle system M23.

The first vibration signal S22 and the second vibration signal S24 are converted from the analog signal into the digital signal by the analog-to-digital converter of the signal processing unit 120, and the noises outside 5~100 Hz are filtered out by the filter of the signal processing unit 120. The operation of the analog-to-digital converting and the noise filtering are changeable without limitations on the operation order.

In step S230, in one embodiment, the analysis unit 140 analyzes a body movement according to the first vibration signal S22 and the second vibration signal S24. In this step, the analysis unit 140 performs the analyzing according to a first signal feature of the first vibration signal S22 and a second signal feature of the second vibration signal S24. The first signal feature and the second signal feature comprise, for example, but not limited to, at least one of an amplitude and a frequency.

For example, step S230 includes step S231~S237. In step S231, in one embodiment, the analysis unit 140 is configured to determine whether a first signal feature of the first vibration signal S22 is greater than or equal to a first predetermined value and a second signal feature of the second vibration signal S24 is less than a second predetermined value. If yes, the analysis unit 140 is configured to perform step S232, else perform step S233.

Figure 8:
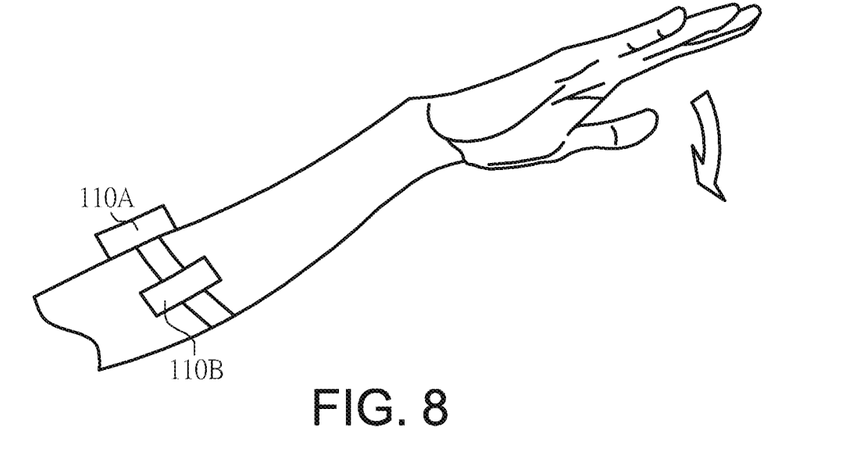
FIG. 8 shows a schematic diagram of a first movement.

In step S232, in one embodiment, the analysis unit 140 determines the analysis result A2 of the body movement is a first movement. In one embodiment, FIG. 8 shows the schematic diagram of the first movement. For example, the analysis unit 140 determines the analysis result A2 is swinging downward if only the first signal feature is significantly greater.

In step S233, in one embodiment, the analysis unit 140 is configured to determine whether a first signal feature of the first vibration signal S22 is less than a third predetermined value and a second signal feature of the second vibration signal S24 is greater than or equal to a fourth predetermined value. If yes, the analysis unit 140 is configured to perform step S234, else perform step S235.

Figure 9:
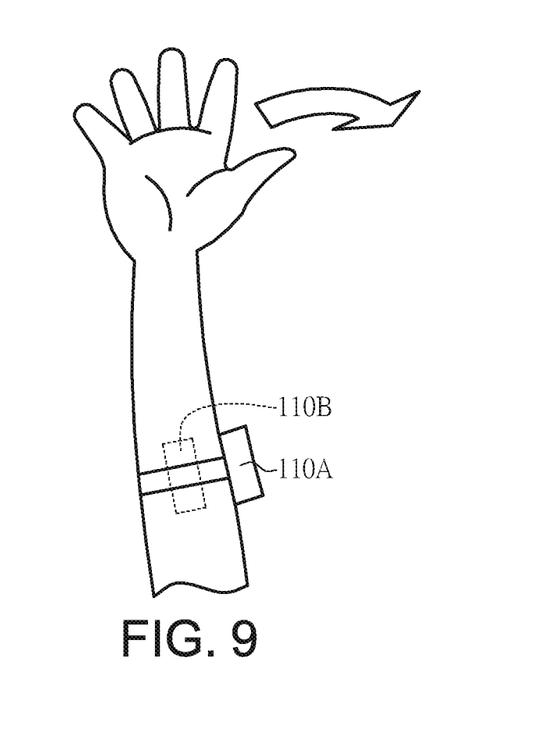
FIG. 9 shows a schematic diagram of a second movement.

In step S234, the analysis unit 140 determines the analysis result A2 of the body movement is a second movement. In one embodiment, FIG. 9 shows the schematic diagram of the second movement. For example, the analysis unit 140 determines the analysis result A2 is swinging right if only the second signal feature is significantly greater.

In step S235, in one embodiment, the analysis unit 140 is configured to determine whether a first signal feature of the first vibration signal S22 is greater than or equal to a fifth predetermined value and a second signal feature of the second vibration signal S24 is greater than or equal to a sixth predetermined value. If yes, the analysis unit 140 is configured to perform step S236, else perform step S237.

In embodiments, the first the sixth predetermined values are designed to the same value. In embodiments, they are designed to different values. In embodiments, some of the predetermined values are different.

Figure 10:
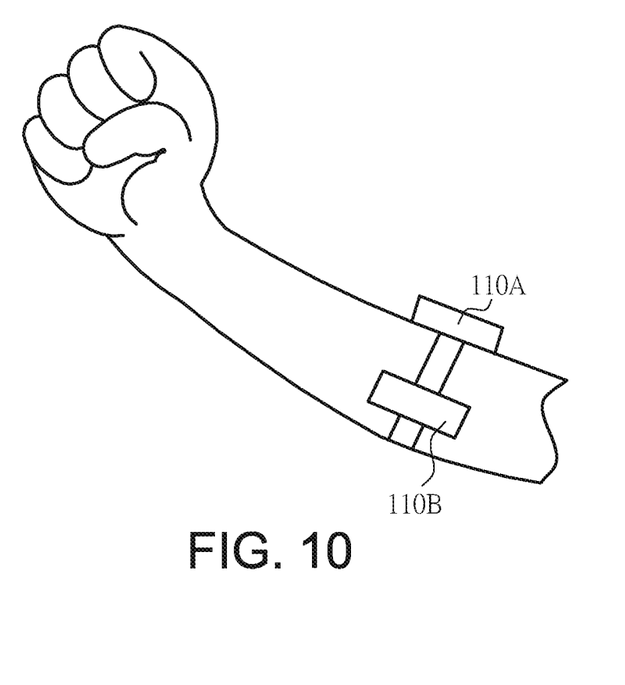
FIG. 10 shows a schematic diagram of a third movement.

In step S236, the analysis unit 140 determines the analysis result A2 of the body movement is a third movement. In one embodiment, FIG. 10 shows the schematic diagram of the third movement. For example, the analysis unit 140 determines the analysis result A2 is making a fist if both of the first signal feature and the second signal feature are significantly greater.

In step S237, the analysis unit 140 is configured to determine there is no movement.

In FIG. 5A, the control unit 920 receives the analysis result A2 from the analysis unit 140. In FIG. 5B, the analysis result A2 may be transmitted to the transmission unit 910 of the electronic device 900B through the transmission unit 160. In FIG. 5C, the control unit 920 receives the analysis result A2 from the analysis unit 940. In step S240, in one embodiment, after the control unit 920 receives the analysis result A2 of the body movement, the control unit 920 performs the command CM2 according to the analysis result A2 of the body movement. The command CM2, such as turn off the TV, answer the phone, or turn off the screen.

In this step, a command mapping table which records the mappings of body movements and commands may be pre-stored in the database 930. The control unit 920 looks up the command CM2 in the command mapping table.

Further, the steps of the disclosed methods may be modified in various ways, including by reordering steps and/or inserting or deleting steps, without departing from the principles of the present disclosure.

Implementations of the various processes and features described herein may be embodied in a variety of different equipment or applications, particularly, for example, equipment or applications associated with detecting muscle activity.

It will be apparent to those skilled in the art that various modifications and variations can be made to the disclosed embodiments. It is intended that the specification and examples be considered as exemplary only, with a true scope and spirit of the disclosure being indicated by the following claims.

What is claimed is:

1. A muscle activity detection system, comprising:
   a wearable ring, having a central point, a first extension line and a second extension line, wherein the first extension line and the second extension pass through the central point and are substantially perpendicular with each other;
   a first vibration sensor, located at a first antagonistic muscle group corresponding to a first agonist muscle system to detect a first vibration signal of the first agonist muscle system for analyzing a body movement, wherein the first antagonistic muscle group and the first agonist muscle system locate two opposite sides of a body region, the first vibration sensor is fixed on the wearable ring, and only the first vibration sensor is located at the first extension line;
   a second vibration sensor, located at a second antagonistic muscle group corresponding to a second agonist muscle system to detect a second vibration signal of the second agonist muscle system for analyzing the body movement, wherein the second antagonistic muscle group and the second agonist muscle system are located on two opposite sides of the body region, the second vibration sensor is fixed on the wearable ring, and only the second vibration is located at the second extension line; and
   an analysis circuit, analyzing the body movement at least according to the first vibration signal and the second vibration signal;
   wherein passes through the first antagonistic muscle group and the first agonist muscle system, the second extension line passes through the second antagonistic muscle group and the second agonist muscle system and crosses the first extension line, only one vibration sensor is located on the first extension line being the first vibration sensor, and only one vibration sensor located on the second extension line being the second vibration sensor.

2. The system according to claim 1, wherein the first vibration signal is a Mechanomyography (MMG) signal.

3. The system according to claim 1, the first agonist muscle system is independent of the second antagonistic muscle group when the first agonist muscle system has a first action, and the second agonist muscle system is independent of the first antagonistic muscle group when the second agonist muscle system has a second action.

4. The system according to claim 1, wherein the first vibration sensor is a sound reception device, an inertial sensing element or a piezoelectric sensing element.

5. The system according to claim 1, wherein the first extension line is perpendicular to the second extension line.

6. The system according to claim 1, wherein if a first signal feature of the first vibration signal is greater than or equal to a first predetermined value, and a second signal feature of the second vibration signal is less than a second predetermined value, the analysis circuit determines that an analysis result of the body movement is a first movement;

if the first signal feature of the first vibration signal is less than a third predetermined value, and the second signal feature of the second vibration signal is greater than or equal to a fourth predetermined value, the analysis circuit determines that the analysis result of the body movement is a second movement; and if the first signal feature of the first vibration signal is greater than or equal to a fifth predetermined value, and the second signal feature of the second vibration signal is greater than or equal to a sixth predetermined value, the analysis circuit determines that the analysis result of the body movement is a third movement.

7. The system according to claim 1, wherein the analysis circuit analyzes the body movement according to a signal feature of the first vibration signal, and the signal feature comprises at least one of an amplitude and a frequency.

8. A method for detecting a muscle activity adapted to a muscle activity detection system, comprising:

wearing a wearable ring having a central point, a first extension line and a second extension line on an arm, wherein the first extension line and the second extension pass through the central point and are substantially perpendicular with each other, a first vibration sensor is fixed on the wearable ring, only the first vibration sensor is located at the first extension line, a second vibration sensor is fixed on the wearable ring, and only the second vibration sensor is located at the second extension line;

detecting a first vibration signal of a first agonist muscle system by the first vibration sensor located at a first antagonistic muscle group corresponding to the first agonist muscle system, wherein the first antagonistic muscle group and the first agonist muscle system locate on two opposite sides of a body region;

detecting a second vibration signal of a second agonist muscle system by the second vibration sensor located at a second antagonistic muscle group corresponding to the second agonist muscle system, wherein the second antagonistic muscle group and the second agonist muscle system are located on two opposite sides of the body region; and analyzing, by an analysis circuit, a body movement at least according to the first vibration signal and the second vibration signal;

wherein passes through the first antagonistic muscle group and the first agonist muscle system, the second extension line passes through the second antagonistic muscle group and the second agonist muscle system and crosses the first extension line, only one vibration sensor is located on the first extension line being the first vibration sensor, and only one vibration sensor located on the second extension line being the second vibration sensor.

9. The method according to claim 8, wherein the first vibration signal comprises a Mechanomyography (MMG) signal.

10. The method according to claim 8, wherein the step of detecting the first vibration signal is performed by using a sound reception device, an inertial sensing element or a piezoelectric sensing element.

11. The method according to claim 8, wherein the first extension line is perpendicular to the second extension line.

12. The method according to claim 8, wherein the step of analyzing the body movement comprises:

determining that an analysis result of the body movement is a first movement, if a first signal feature of the first vibration signal is greater than or equal to a first predetermined value, and a second signal feature of the second vibration signal is less than a second predetermined value;

determining that the analysis result of the body movement is a second movement, if the first signal feature of the first vibration signal is less than a third predetermined value, and the second signal feature of the second vibration signal is greater than or equal to a fourth predetermined value; and determining that the analysis result of the body movement is a third movement, if the first signal feature of the first vibration signal is greater than or equal to a fifth predetermined value, and the second signal feature of the second vibration signal is greater than or equal to a sixth predetermined value.

13. The method according to claim 8, wherein the step of analyzing the body movement is performed according to a signal feature of the first vibration signal, and the signal feature comprises at least one of an amplitude and a frequency.

* * * * *